United States Patent [19]

Spencer

[11] Patent Number: 6,071,690

[45] Date of Patent: Jun. 6, 2000

[54] IONOMERIC MODIFIED POLY-ETHER-ESTER PLASTIC CONTAINER FOR CRYOGENIC FLUIDS

[75] Inventor: Dudley W. C. Spencer, Wilmington, Del.

[73] Assignee: Denco, Inc., Wilmington, Del.

[21] Appl. No.: 09/017,219

[22] Filed: Feb. 2, 1998

[51] Int. Cl.[7] .................................................. C12N 5/00
[52] U.S. Cl. .............................. 435/2; 435/374; 62/64; 428/35.2; 428/36.92
[58] Field of Search ........................... 435/374, 2; 62/64; 428/35.2, 36.92

[56] References Cited

U.S. PATENT DOCUMENTS

| | | |
|---|---|---|
| 4,010,222 | 3/1977 | Shih . |
| 4,048,254 | 9/1977 | Hillier et al. . |
| 4,219,628 | 8/1980 | Weemes et al. . |
| 4,251,995 | 2/1981 | Pert et al. . |
| 4,322,335 | 3/1982 | Nield . |
| 4,337,947 | 7/1982 | Saito et al. . |
| 4,344,874 | 8/1982 | Akagi et al. . |
| 4,616,064 | 10/1986 | Zukosky et al. . |
| 4,628,072 | 12/1986 | Shiraki et al. . |
| 4,657,970 | 4/1987 | Shiraki et al. . |
| 4,670,510 | 6/1987 | Kobayashi et al. . |
| 4,680,344 | 7/1987 | Coker . |
| 4,778,842 | 10/1988 | Taniguchi et al. . |
| 4,806,588 | 2/1989 | Fujimoto et al. . |
| 4,816,343 | 3/1989 | Mueller et al. . |
| 4,820,768 | 4/1989 | Shiraki et al. . |
| 4,861,830 | 8/1989 | Ward, Jr. . |
| 4,868,243 | 9/1989 | Gelles et al. . |
| 4,906,687 | 3/1990 | Modic . |
| 4,914,152 | 4/1990 | Miyashita et al. . |
| 4,950,717 | 8/1990 | Seymour et al. . |
| 4,954,568 | 9/1990 | Gelles et al. . |
| 4,968,464 | 11/1990 | Kojoh et al. . |
| 5,089,553 | 2/1992 | Umeda et al. . |
| 5,091,459 | 2/1992 | Howe . |
| 5,112,915 | 5/1992 | Morelli et al. . |
| 5,115,012 | 5/1992 | Howe . |
| 5,453,099 | 9/1995 | Lee et al. . |
| 5,496,291 | 3/1996 | Spencer . |
| 5,578,028 | 11/1996 | Drago et al. . |
| 5,733,268 | 3/1998 | Spencer . |
| 5,919,173 | 7/1999 | Spencer . |
| 5,928,216 | 7/1999 | Spencer . |

OTHER PUBLICATIONS

2244 Research Disclosure (1989) May, No. 301, New York, US "*Blends of Polyester–Ethers with Ethylene–Acrylic Acid Copolymers*".

*Primary Examiner*—Leon B. Lankford, Jr.
*Attorney, Agent, or Firm*—Connolly Bove Lodge Hutz LLP

[57] ABSTRACT

Plastic articles made of ionomeric modified poly-ether-ester are stored in a cryogenic fluid containing receptacle. The articles may be tubing or bags or articles of surgical equipment or clothing.

16 Claims, 1 Drawing Sheet

IONOMERIC MODIFIED POLY-ETHER-ESTER PLASTIC CONTAINER FOR CRYOGENIC FLUIDS

CROSS-REFERENCE TO RELATED APPLICATIONS

This application relates to variations of the inventions disclosed in my U.S. Pat. No. 5,496,291 and in my co-pending application Ser. No. 803,779, filed Feb. 24, 1997; Ser. No. 790,192, filed Jan. 30, 1997 now, U.S. Pat. No. 5,928,216 and Ser. No. 742,,046, filed Nov. 1, 1996 now, U.S. Pat. No. 5,733,268.

BACKGROUND OF THE INVENTION

Polyvinylchloride (PVC) is the accepted material for use as tubing in various medical applications, such as peritoneal dialysis, blood processing, chemotherapy and other uses. In such uses, a consumable is conveyed through the tubing from one location to another. For peritoneal dialysis (CAPD), for example, it is also the practice to replace a used dialysate bag with a new bag. This is accomplished by cutting through the PVC tubing leading from the used bag and then welding tubing from a new bag to the cut portion of the tubing so that one bag may replace another. PVC is also the generally accepted material for forming bags and other medical containers and is commonly used as tubing in food processing particularly for fluids and semi-solids. In addition, PVC is the material generally used for forming sheets and films for bacterial and virus exclusion. Despite its acceptance by the art, PVC has a number of disadvantages which would be desirable to overcome in such uses. For example, conventional PVC includes a plasticizer (DOP) which might leach into the solutions in the bag. Further, after PVC has leached its DOP, large volumes of PVC particulates are released. Other disadvantages will be later referred to.

In my U.S. Pat. No. 5,496,291 and application Ser. No. 08/803,779, filed Feb. 24, 1997, I disclose an ionomeric modified poly-ether-ester material which could be used as a substitute for polyvinylchloride. Other variations of that material are disclosed in application Ser. No. 08/742,046, filed Nov. 1, 1996 now, U.S. Pat. No. 5,733,268 and Ser. No. 08/790,192, filed Jan. 30, 1997 now, U.S. Pat. No. 5,928, 216.

SUMMARY OF THE INVENTION

An object of this invention is to provide a material which will act as an improved replacement for PVC in the conventional uses of PVC.

A further object of this invention is to provide such a material which can be used 1) as tubing for medical applications, 2) as bags and other medical containers, 3) as surgical equipment or clothing such as gloves, drapes, aprons, boots, gowns and face masks, 4) for tubing in food processing and 5) as sheets and films for bacterial and virus exclusion.

A still further object of this invention is to provide techniques for storing devices made from such material.

In accordance with this invention the material which meets the above objects includes an ionomeric modified poly-ether-ester as generally described in my U.S. Pat. No. 5,496,291 and in my above noted patent application. In the practice of this invention the various devices made from the material are cryogenically stored. I have found that such manner of storing the devices expands the possible uses of the devices without. detriment to their physical characteristics. Thus, for example, the devices can be used in connection with storing items such as semen, blood cells and DNA. I have also found that by cryogenically storing the devices it is not necessary to include as much ionomer with the poly-ether-ester as in the amounts disclosed in my '291 patent and the above noted patent applications.

THE DRAWINGS

DETAILED DESCRIPTION

Figure 1:
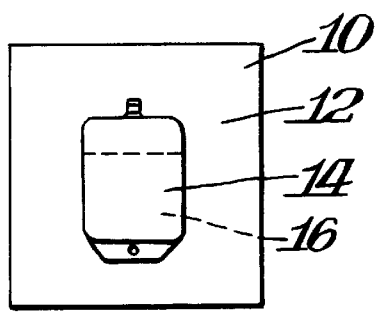
FIG. 1 is a front elevational view showing the practice of the invention wherein a device made by the material of this invention is cryogenically stored.
Figure 3:
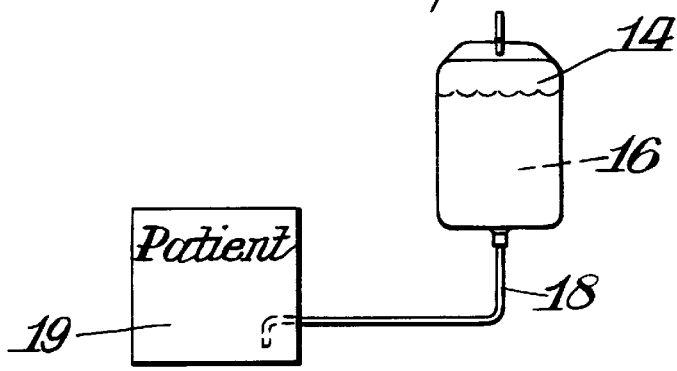
FIG. 3 is a schematic view showing a bag and tube assembly in accordance with this invention used for peritoneal dialysis.

The present invention is directed to providing a material which can be used as a substitute for PVC in the conventional uses of PVC while having advantages over such PVC material. The material of this invention is an ionomeric modified poly-ether-ester with a small amount of ionomer. Poly-ether-ester is a well known material generally used to take advantage of its high strength characteristics. Such material is used, for example, in clothing generally referred to as polyester clothing. Ordinarily, the strength of such material would make it unsuitable for use as a substitute for PVC in the uses of PVC with which this invention deals. It has been discovered, however, that the poly-ether-ester material can be modified by incorporation of a small amount of an ionomer which would modify the characteristics of the poly-ether-ester by giving it sufficient fragility to, for example, permit the material when used as a sealed tube to pop open. The specific amount of ionomer would depend upon the end use. The qualities may also be retained when the material is mixed with a small amount of silica, such as colloidal silica dioxide (amorphous or pharmaceutical grade). The silica may be in the form of silica oil.

The present invention is based upon variations of the material disclosed in my '291 patent and the patent applications noted above. All of the details of the '291 patent and the above noted patent applications are incorporated herein by reference thereto. In general, my patent and applications disclose an ionomeric modifier which comprises from 0.5–50% by weight and preferably from 1% to 25% by weight of the combination depending upon the end use requirement. For example, in tubing such as for CAPD use where the material is to be sealed, welded and the lumen reopened the broad ionomer composition range would be 2% to 15% by weight, a more preferred range of 3%–10% by weight. A range of 7–10% by weight is ideal. The result is a tube which is strong, sufficiently rubber like, and a degree of fracture to make reopening of the sealed tubes by finger pressure. For bags, films and other thin structures the ionomer would be present in a range of from 1% to 50% by weight of the combination depending on the end use requirements. For food processing tubes and aseptic surgical draping procedures a range of 10% to 20% by weight is desirable. For implanted catheters and sutures the range of 0.5 to 1% by weight is preferred.

The material of my prior invention in Ser. No. 08/742,046 is a combination of PVC and an ionomeric modified polyether-ester wherein the material has from 0.5 to 25% by weight PVC, from 1% to 50% by weight ionomer and from 50% to 99% by weight poly-ether-ester with equal mixtures of ionomer and poly-ether-ester being feasible.

The material of my prior invention in Ser. No. 08/790,192 is a combination of silica and an ionomeric modified poly-ether-ester wherein the material has from 5% to 10% by weight silica oil or from 1% to 3% by weight colloidal silica dioxide mixed with from 1% to 50% by weight ionomer and from 50% to 99% by weight poly-ether-ester with equal mixtures of ionomer and polyether-ester being feasible.

The basic material components are as follows:
Poly-ether-ester
POLY-ETHER-ESTER BLOCK COPOLYMER (Block poly-ether-ester) (Co-poly-ether-ester) (Polyester elastomer) (Thermoplastic polyether-ester) Tradenames: Hytrel, Lomod, Pelprene and others. A block copolymer containing both poly-ether and ester blocks. The best known example is poly-(tetramethyleneterephthalate-b-poly-oxytetramethyleneterephthalate).
Ionomer
IONOMER Trade name Surlyn, among others. A copolymer of ethylene with 1–10% by weight methacrylic acid, which has been converted to methacrylate salt, often the sodium, magnesium or zinc salt, by neutralization with the appropriate base. The resultant ionic groups tend to aggregate to form domains which act as physical crosslinks for the polyethylene. However, the domains break down on heating, so the material may be melt processed as other thermoplastics. The copolymers are produced by the high pressure ethylene polymerization process and so are similar to low density polyethylene. The copolymer decreases crystallinity but consequent loss of stiffness is restored by the physical crosslinks. The material is more transparent than LDPE and shows better adhesion, which makes it useful as a layer in laminated coextruded packaging films and in, therefore, homogenous mixing.

Reference is made to U.S. Pat. No. 5,496,291 all of the details of which are incorporated herein by reference thereto for a further disclosure of the ionomeric modified poly-ether-ester component of the material.

Poly-ether-esters are valuable materials because they have excellent low temperature properties (freezing) and are impervious to chemicals, oils and tissue. They have one serious negative, however, for many end-uses: They stretch 7× their length under low stress. For example, a tube one foot long will stretch to seven feet before breaking. Industrial goods such as bags, films, tubes, etc. readily warp out of shape and become unacceptable as end-use products. The present invention adds an ionomer to the composition to make useful, thin products.

Ionomers are somewhat like polyethylene in that they are useful as films because they are excellent for food wrapping, medical and pharmaceutical packing and are impervious to most oils and chemicals. Like polyethylene, they puncture readily and only stretch 3× before fracture.

A common use is a coating over stronger materials and are frequently used as a co-extrusions on nylon and other films to provide heat sealing.

The invention makes use of the fact that poly-ester-ethers and ionomers can be selected which melt at the same temperature (191° C.) or at sufficiently close temperatures. Instead of a coating, the invention mixes them together. In this way, the negatives of the two materials could be adjusted in a variety of ways to make new materials that are stronger than the ionomers, and less stretchy than the poly-ether-esters.

Combining the two materials as described also reduces another major limitation of the poly-ester-ethers (P.E.E.). They can absorb excessive moisture depending upon temperature and humidity. In the case of P.E.E. use in autoclaved (steam sterilized) medical tubing for example, the moisture pick-up makes the tubing unacceptable for further processing. Adding 5% to 7% ionomer to the composition reduces the moisture absorbance to less than 1% by weight. A level comparable to medical grade PVC and well within the limits required for TCD® to welding.

For forming the material of this invention the following process may be used. The individual materials are fed separately in pellet form into a single screw extruder. Other forms of extruders could be used satisfactorily but a single screw is sufficient and simpler to control. The materials in pellet streams are mixed to the required ratios and fed into the extruder. Extrusion rates of 10 to 250 lbs per hour are practical at melt temperatures of 180° C. to 200° C., with 191° C. being ideal. The melt is fed through a sizing die and liquid quenched as it exits the die for accuracy and handling purposes.

A typical extruder heating and mixing profile would involve feeding the materials, such as in pellets, from individual feed hoppers into the extruder where the feed zone of the extruder is at 300° F. The material would then pass to a compression zone at 350° F. The materials would then pass into a melting zone at 375° F. Finally, the material would be extruded into the desired shapes. Techniques such as conventionally used for PVC could then be used for forming the end products.

In general, the portion of the material having the ionomer and poly-ether-ester may include from 10–15% by weight of the ionomer when used for bags (containers), tubing and films for medical, surgical or food processing uses. The range of ionomer of the portion of the material having the ionomer and poly-ether-ester may include from 5–15% of the ionomer when used for surgical equipment and clothing such as gloves, drapes, aprons, face masks, boots and gowns.

The present invention is directed to a manner of storing the articles or devices made from such material. I have found that when the articles or devices are cryogenically stored it is possible to reduce the amount of the ionomer in the material without detrimentally affecting the desired characteristics. If the amount of ionomer is relatively large, such as at the upper limits of the various ranges disclosed in my '291 patent and patent applications the presence of such an amount of ionomer may cause cracking. Where, however, the devices or articles are cryogenically stored, that amount of ionomer could be significantly reduced. For example, when used for tubes, bags and films, the ionomer may be present in a range of 0.05–2% by weight of the portion of the material containing the poly-ether-ester and the ionomer. The range could be increased at some sacrifice to properties such as to 5% by weight ionomer or the range could be decreased to 0.01% and even to the point of eliminating the ionomer. Thus, in the preferred practice of the invention there is no more than 2% by weight of the ionomer in the portion of the material having poly-ether-ester and any ionomer. The same ranges could be used for end products, such as gloves, drapes, aprons, boots, gowns and face masks. The material could also include small amounts of silica and/or PVC in the amounts disclosed in my patent applications added to the combined poly-ether-ester and ionomer.

FIG. 1 illustrates a practice of the invention wherein a storage receptacle 10 containing a cryogenic material 12 is used for storing a bag or container 14 having a substance such as semen, blood cells or DNA 16 stored in the bag 14. Bag 14 is made with the material of this invention. Any suitable cryogenic, such as liquid nitrogen, carbon dioxide or helium could be used.

Figure 2:
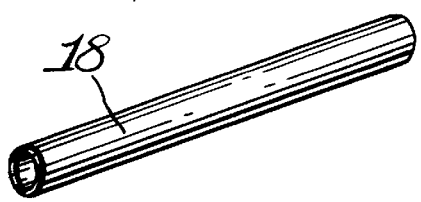
FIG. 2 is a perspective view showing a tube which can be used in the practice of this invention.
Figure 6:
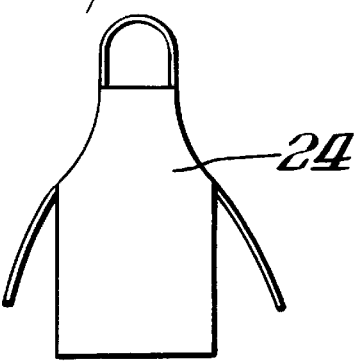
FIG. 6 is a top plan view of an apron in accordance with this invention.
Figure 4:
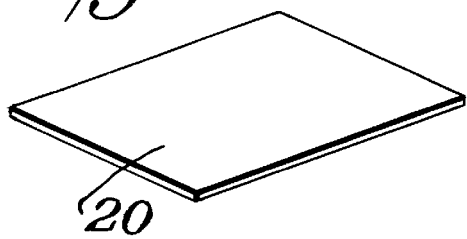
FIG. 4 is a top plan view of a surgical drape or film in accordance with this invention.
Figure 7:
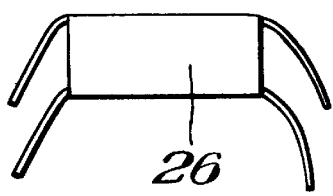
FIG. 7 is a top plan view of a surgical face mask in accordance with this invention.
Figure 5:
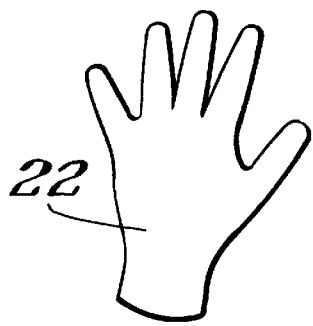
FIG. 5 is a top plan view of a surgical glove in accordance with this invention.

Other types of devices which may be stored include, for example, tubing 18 of FIG. 2, surgical drapes or films 20 of FIG. 4, gloves 22 of FIG. 5, apron 24 of FIG. 6 cr face mask 26 of FIG. 7. Similarly, surgical boots or gowns may be stored. It is desirable to store such devices particularly when sterility of storage is preferred by having the various devices stored in a sterile condition within a cryogenic receptacle. The invention may broadly be practiced by cryogenically storing any device made of the material of this invention which is a substitute for such a device being previously made of PVC.

FIG. 2 shows the combination of a container or bag 14 used with tubing 18 leading to a patient 19 for CAPD use. Both the bag and tubing would have been cryogenically stored.

A series of cryogenic tests were performed on tubing such as tube 18 using liquid nitrogen at −273° C. The tubing material had an outside diameter of 5.4 mm and an inside diameter of 3.85 mm. The tubing was of CAPD size being 30 cm long and was bent in a U-shape, then immersed in a thermos-bottle of liquid nitrogen. The tube was removed from the Dewar and dropped 3 feet to a concrete floor. The material did not shatter as most plastics do, but remained intact and resilient.

A second test was performed using the same piece of tubing. In the second test the U-shaped tube was pulled to straighten out the tube. Remarkably the tube was flexible enough to straighten without shattering or cracking. After returning to room temperature the tube integrity was completely restored. The invention is particularly useful in that it has applicability for the storage of many biological fluids such as mammalian cell culturing processes which require cryogenic storage capability. Advantageously, the material of this invention is capable of withstanding the rigors of cryogenic temperatures such as the temperatures of liquid nitrogen and still remain flexible.

Even with the reduced amount of ionomer in accordance with this invention, where the tubing is cryogenically stored the tubing material is capable of being welded to itself to form a seal which resists opening at internal pressure of up to 60 psi with the seal being capable of opening under external finger pressure. The tubing is also capable of being welded to a conventional PVC tube. Where the material is used in a container or bag the container can be sterilized. Where used for tubing and containers, the invention may be practiced in such assemblies as a peritoneal dialysis assembly (FIG. 2), where the container 14 is the dialysate bag mounted at a location remote from the patient and the tubing 18 is mounted to connecting structure of the container to permit the flow of fluid between the container and the patient 19.

The invention may also be practiced in a urinary drainage assembly where the container is a urinary container and the tubing conveys urine from the patient to the container.

The invention may be practiced in a blood processing assembly which includes a blood supply needle and a blood collecting container wherein the container is made in accordance with the material of this invention and the tubing creates flow communication between the needle and the container.

The invention may also be practiced in a chemotherapy assembly where the container is a solution container and the tubing leads from the container to a patient to deliver the solution to the patient and with a drug introducing assembly communicating with the tubing to introduce a drug into the solution.

The invention may be practiced in a parenteral feeding assembly wherein the container is a liquid nutrient container and the tube is inserted into the sub-clavian drain of a patient in flow communication with the container.

The invention may be practiced in a cell culturing assembly which includes a reactor with the tubing leading from the reactor.

In addition to the above described medical type uses, the invention may also be used in food processing particularly as tubing for fluids and semi-solids and as the material for making sheets and films for bacterial and virus extrusion. When used as sheets or films, the sheet could be draped over the patient and the surgeon would cut through the sheet into the patient.

As is apparent the invention can be practiced for PVC-substitute articles of any type wherein the article is cryogenically stored.

What is claimed is:

1. In combination, a storage receptacle, a cryogenic fluid in said storage receptacle, a plastic article disposed in said cryogenic fluid for being stored in said receptacle, and said plastic article being made of a plastic material which is an ionomeric modified poly-ether-ester containing no more than 5% by weight ionomer, said poly-ether-ester and said ionomer individually and in combination being plasticizer-free, said plastic article being hollow to create a storage chamber, and a substance to be preserved in said hollow chamber.

2. The combination of claim 1 wherein said material contains no more than 2% by weight ionomer.

3. The combination of claim 2 wherein the material contains at least 0.01% by weight ionomer.

4. The combination of claim 3 wherein said plastic article is tubing.

5. The combination of claim 3 wherein said plastic article is a container.

6. The combination of claim 5 wherein said substance in a human material selected from the group consisting of semen, blood cells and DNA.

7. The combination of claim 2 wherein said plastic material contains up to 10% by weight of silica.

8. The combination of claim 2 wherein said plastic material containers from 0.5 to 25% by weight of PVC.

9. A method of preserving substances comprising the steps or providing a storage receptacle, inserting a cryogenic fluid in the storage receptacle, inserting the plastic article in the cryogenic fluid with the plastic article being made from poly-ether-ester material which is an ionomeric modified poly-ether-ester containing no more than 5% by weight ionomer, the poly-ether-ester and the ionomer individually and in combination being plasticizer-free, the plastic article being hollow to create a hollow chamber, and inserting the substances to be preserved into the hollow chamber prior to inserting the plastic article in the cryogenic fluid so that the substance is within the plastic article while the plastic article is in the cryogenic fluid.

10. The method of claim 9 wherein the plastic material contains at least 0.01% by weight ionomer.

11. The method of claim 10 wherein the plastic article is tubing.

12. The method of claim 10 wherein the plastic article is a container.

13. The method of claim 12 wherein human substances are in the container.

14. The method of claim 9 wherein the substance is semen.

15. The method of claim 9 wherein the substance is blood.

16. The method of claim 9 wherein the substance is DNA.

* * * * *